US009670112B2

(12) United States Patent
Vivien et al.

(10) Patent No.: US 9,670,112 B2
(45) Date of Patent: Jun. 6, 2017

(54) PROCESS FOR THE PRODUCTION OF KEROSENE FROM BUTANOLS

(71) Applicant: IFP ENERGIES NOUVELLES, Rueil-Malmaison (FR)

(72) Inventors: Tom Vivien, Lyons (FR); Vincent Coupard, Villeurbanne (FR); Francois Hugues, Charly (FR); Raphael Huyghe, Saint Andeol le Chateau (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/427,363

(22) PCT Filed: Sep. 6, 2013

(86) PCT No.: PCT/FR2013/052054
§ 371 (c)(1),
(2) Date: Mar. 11, 2015

(87) PCT Pub. No.: WO2014/041285
PCT Pub. Date: Mar. 20, 2014

(65) Prior Publication Data
US 2015/0246855 A1 Sep. 3, 2015

(30) Foreign Application Priority Data
Sep. 12, 2012 (FR) ...................................... 12 02429

(51) Int. Cl.
| *C10G 69/12* | (2006.01) |
| *C10L 1/04* | (2006.01) |
| *C07C 2/10* | (2006.01) |
| *C07C 1/24* | (2006.01) |
| *C10G 45/00* | (2006.01) |
| *C10G 50/00* | (2006.01) |

(52) U.S. Cl.
CPC ................. *C07C 1/24* (2013.01); *C07C 2/10* (2013.01); *C10G 45/00* (2013.01); *C10G 50/00* (2013.01); *C10G 69/126* (2013.01); *C10L 1/04* (2013.01); *C07C 2521/12* (2013.01); *C10G 2300/1011* (2013.01); *C10G 2400/02* (2013.01); *C10G 2400/04* (2013.01); *C10G 2400/08* (2013.01); *C10L 2200/0469* (2013.01); *C10L 2290/08* (2013.01); *C10L 2290/10* (2013.01); *C10L 2290/543* (2013.01); *Y02P 30/20* (2015.11)

(58) Field of Classification Search
CPC ........................................................ C07C 2/18
USPC ........ 585/255, 326, 517, 254, 315, 638, 733
See application file for complete search history.

(56) References Cited

U.S. PATENT DOCUMENTS

| 3,219,574 | A | * | 11/1965 | Schneider | ............... | C10G 65/12 |
| | | | | | | 208/108 |
| 6,441,261 | B1 | * | 8/2002 | Kuechler | .................. | C07C 1/20 |
| | | | | | | 585/639 |
| 7,572,946 | B2 | | 8/2009 | Lacombe et al. | | |
| 8,067,655 | B2 | | 11/2011 | Nichols et al. | | |
| 8,487,149 | B2 | | 7/2013 | Gruber et al. | | |
| 2006/0135832 | A1 | | 6/2006 | Vora et al. | | |
| 2007/0015945 | A1 | * | 1/2007 | Louret | .................. | C10G 50/00 |
| | | | | | | 585/329 |
| 2009/0299109 | A1 | * | 12/2009 | Gruber | ...................... | C10L 1/04 |
| | | | | | | 585/14 |
| 2009/0299117 | A1 | | 12/2009 | Nichols et al. | | |
| 2012/0259146 | A1 | | 10/2012 | Gruber et al. | | |
| 2012/0323055 | A1 | | 12/2012 | Gruber et al. | | |
| 2014/0163267 | A1 | | 6/2014 | Gruber et al. | | |

FOREIGN PATENT DOCUMENTS

| BE | EP 2366682 A1 * | 9/2011 | ............. | B01J 29/65 |
| WO | 2009/079213 A2 | 6/2009 | | |
| WO | 2009/145861 A1 | 12/2009 | | |

OTHER PUBLICATIONS

International Search Report dated Oct. 30, 2013 issued in corresponding PCT/FR2013/052054 application (pp. 1-3).

* cited by examiner

*Primary Examiner* — In Suk Bullock
*Assistant Examiner* — Aaron Pierpont
(74) *Attorney, Agent, or Firm* — Millen White Zelano and Branigan, PC; John Sopp; Anthony Zelano

(57) ABSTRACT

A process for the production of middle-distillate hydrocarbon-containing bases from a butanol feedstock, comprising: a) isomerizing dehydration of butanol feedstock; b) separating the water from butylenic effluent; c) purifying the organic liquid effluent from stage b); d) oligomerizing a feedstock that comprises at least a portion of the purified organic effluent from stage c), the entire effluent from stage g), and at least a portion of the light product from stage f); e) oligomerizing the first oligomerization effluent to produce a second oligomerization effluent; f) fractionating the second oligomerization effluent into at least three products: a light product mostly comprising $C_2$ to $C_4$ compounds, an intermediate product mostly comprising $C_5$ to $C_9$ compounds, and a middle distillate product mostly comprising compounds having at least 10 carbon atoms; g) oligomerizing at least a portion of the intermediate product, and h) hydrogenating at least a portion of the middle distillate product.

9 Claims, No Drawings

PROCESS FOR THE PRODUCTION OF KEROSENE FROM BUTANOLS

TECHNICAL FIELD OF THE INVENTION

This invention relates to the transformation of butanol, and more particularly biobutanol, into a fuel base.

It relates more particularly to a flexible catalytic process for transformation of butanol into middle distillates.

PRIOR ART

The demand for use of renewable resources as a partial replacement for petroleum resources for the synthesis of fuels continues to grow. Thus, the use of biobutanol in the synthesis of bases for fuels is gaining more and more active interest.

Biobutanol is defined as a butanol that is produced from renewable resources obtained from biomass, such as, for example, the lignocellulosic raw materials.

The latter are cellulosic materials, i.e., that consist of more than 90% by weight of cellulose, and/or lignocellulosic materials, i.e., that consist of cellulose, hemicelluloses, which are polysaccharides that essentially consist of pentoses and hexoses, as well as lignin, which is a macromolecule of complex structure and of high molecular weight, composed of aromatic alcohols connected by ether bonds.

The emergence of projects for production of biobutanol is broadly supported by the public and industrial push to develop second-generation biofuels, over time upgrading a vast array of lignocellulosic raw materials.

By comparison with ethanol, n-butanol and isobutanol have several advantages: higher energy density; less hydrophilic nature; better compatibility, both with the storage/transport infrastructures of fuels and with existing automobile engines; lower vapor pressures; less corrosive. Isobutanol is particularly compatible with diesel fuel whereas n-butanol is miscible with gasoline.

N-butanol is one of the products of fermentation called ABE (acetone-butanol-ethanol) of *Clostridium acetobutylicum*. Recent projects use selected strains, mutant or OGM, making possible a specific production of n-butanol, one of the limiting factors being its toxicity for the microorganisms in question. More tolerant strains and continuous or semi-continuous extraction processes are therefore necessary. The bacteria that are used in these processes are always of the genus *Clostridium*.

Isobutanol, or 2-methylpropan-1-ol, is a branched isomer of n-butanol. It is also a product of the fermentation of carbohydrates. Its paths of biosynthesis are, however, different from those of n-butanol. The processes for the production of isobutanol are being developed by players such as Gevo or Butamax from bacterial sources that are different from those used for the production of n-butanol (*E. coli*).

The patent application WO2009/079213 describes the production of bases for fuels from biomass comprising stages of fermentation into alcohol, dehydration of a portion of said alcohols into olefins, oligomerization of a portion of said olefins, and optional hydrogenation of the product of the oligomerization. By contrast, the patent does not propose a means of monitoring the temperature rise in the reactor due to the exothermicity of the oligomerization reaction. The oligomerization is carried out in a single stage.

The patent application WO2011/140560 describes the production of a kerosene base from lignocellulosic raw materials by taking an isobutanol path. Said raw materials are fermented under specific conditions suitable for the production of isobutanol. The latter is next dehydrated and then oligomerized for producing a fraction that is close to kerosene. This application addresses neither the problem of monitoring the temperature rise in the reactor due to the exothermicity of the oligomerization nor the problem of monitoring the composition of the products that are obtained.

OBJECT AND ADVANTAGE OF THE INVENTION

This invention relates to a process for the production of middle-distillate hydrocarbon-containing bases from a butanol feedstock, with said process comprising at least:

a) A stage for isomerizing dehydration of said butanol feedstock in the presence of an amorphous or zeolitic acid catalyst in at least one reactor, operating at an absolute pressure at the reactor inlet of between 0.5 and 1.2 MPa and at a temperature at the reactor inlet of between 350 and 450° C. in such a way as to produce an effluent that is for the most part butylene, b) A stage for separation of the water that is present in said butylenic effluent operating at a pressure of between 0.5 and 1.2 MPa and at a temperature of between 35 and 60° C., c) A stage for purification of the organic liquid effluent that comes from stage b) in such a way as to produce a purified organic effluent, d) A first stage for oligomerization of a feedstock that comprises at least a portion of the purified organic effluent that comes from stage c), the entire effluent that comes from stage g), and at least a portion of the light product that comes from stage 0 in the presence of an amorphous catalyst in at least one reactor that operates at an absolute pressure of between 0.5 and 10 MPa, at a temperature of between 40 and 110° C., and at an hourly volumetric flow rate of between 0.1 and 10 h$^{-1}$, in such a way as to produce a first oligomerization effluent, comprising at least 50% by weight of olefins having a number of carbon atoms that is greater than or equal to 8, with the percentage by weight being expressed relative to the total mass of olefins contained in said effluent, e) A second stage for oligomerization of said first oligomerization effluent, in the presence of an amorphous catalyst in at least one reactor that operates at an absolute pressure of between 2 and 15 MPa, at a temperature of between 100 and 200° C., and at an hourly volumetric flow rate of between 0.1 and 10 h$^{-1}$, in such a way as to produce a second oligomerization effluent, f) A stage for fractionation of said second oligomerization effluent into at least three products that correspond respectively to a light product that for the most part comprises the $C_2$ to $C_4$ compounds, an intermediate product that for the most part comprises the $C_5$ to $C_9$ compounds, and a middle distillate product that for the most part comprises the compounds that have at least 10 carbon atoms, g) A third stage for oligomerization of at least a portion of said intermediate product in the presence of an amorphous catalyst in at least one reactor that operates at an absolute pressure of between 2 and 15 MPa, at a temperature of between 100 and 200° C., and at an hourly volumetric flow rate of between 0.1 and 5 h$^{-1}$, and h) A stage for hydrogenation of at least a portion of said middle distillate product in the presence of a catalyst that comprises at least one metal of group VIII in at least one reactor that operates at an absolute pressure of between 2 and 4 MPa, at a temperature of between 100 and 350° C., and at an hourly volumetric flow rate of between 1 and 5 $h^{-1}$ with a hydrogen to hydrocarbon $H_2/HC$ molar ratio of between 10 and 450.

One advantage of the invention is a better monitoring of the products that are obtained, by the separation of the two oligomerization stages, with said separation also making it possible to limit the temperature rise in the reactor due to the exothermicity of the reactions in each of said stages.

Another advantage of the invention is that it is possible to add aromatic compounds to the fuel base that is produced in accordance with the invention up to the limits provided by the standard ASTM D7566-11a while taking into account the density specification of said standard.

DETAILED DESCRIPTION OF THE INVENTION

Feedstock

The feedstock that is treated in the process according to the invention is a butanol feedstock, with the term butanol characterizing all of the alcohols comprising 4 carbon atoms. Said butanol feedstock is advantageously a biobutanol feedstock, i.e., a butanol feedstock that is produced from renewable resources that come from the biomass. Said butanol feedstock for the most part comprises butanol, at a level of more than 50% by weight, and preferably more than 70% by weight, and it also comprises water, at a content of between 0 and 50% by weight, preferably between 0% and 30% by weight, and in a preferred manner between 15% and 25% by weight; a content of cationic impurities such as, for example, the ions $Na^+$, $Ca^{2+}$, $K^+$, $MN^{2+}$, $Fe^{2+}$, $Cu^{2+}$, $Zn^{2+}$, advantageously less than 0.1% by weight; a content of anionic impurities such as, for example, the ions of chloride, sulfate, nitrite, nitrate, phosphate, advantageously less than 0.1% by weight; a content of metals such as nickel, chromium, and potassium, advantageously less than 0.1% by weight; a content of other alcohols such as, for example, methanol and ethanol, advantageously less than 10% by weight, and preferably less than 5% by weight; a content of oxidized compounds other than the alcohols, such as, for example, ethers, acids, ketones, aldehydes, acetals and esters, advantageously less than 1% by weight; and a content of nitrogen-containing compounds and sulfur-containing compounds, such as, for example, amines, acetonitriles, nitric sulfates, and carbon sulfide, advantageously less than 0.5% by weight, with the percentages by weight being expressed relative to the total mass of said butanol feedstock.

The process according to the invention advantageously comprises a purification stage that is carried out prior to the dehydration stage a) in such a way as to eliminate the cationic and anionic impurities as well as at least a portion of the oxidized compounds for limiting the deactivation of the dehydration catalyst placed downstream.

Said purification stage is advantageously implemented by means that are known to one skilled in the art, such as, for example, the use of at least one resin, the adsorption of impurities, and oxidized compounds on solids that are selected from among molecular sieves, activated carbon, alumina, and zeolites, and the distillation for producing a purified butanol feedstock that responds to levels of impurities that are compatible with the dehydration catalyst and a product that comprises the organic impurities.

Said levels of impurities that are compatible with the dehydration catalyst are a content of ionic impurities of less than 100 ppm, a metal content of less than 50 ppm, a content of oxidized impurities of less than 150 ppm, and a content of nitrogen-containing and sulfur-containing compounds of less than 30 ppm.

A pretreatment stage can also advantageously be implemented by hydrogenation of the oxidized unsaturated compounds in the presence of a nickel-based catalyst, with said pretreatment stage being implemented before or after the purification stage and preferably after.

Dehydration Stage a)

In accordance with the invention, the butanol feedstock, optionally purified, undergoes an isomerizing dehydration stage a) in such a way as to produce an effluent that is for the most part butylene, with operating in the presence of a dehydration catalyst that is known to one skilled in the art, in particular an amorphous acid catalyst or a zeolitic acid catalyst in at least one reactor.

An effluent that is for the most part butylene is defined as an effluent that comprises water and at least 95%, preferably at least 97%, and in a preferred manner at least 98%, by weight of butenes relative to the total mass of the carbon-containing compounds that are present in said effluent that is produced by said stage a). In addition to the majority presence of butenes, said carbon-containing effluent can also comprise other compounds that contain hydrocarbons, hydroxycarbons or oxycarbons in a very minor proportion. In particular, said carbon-containing effluent advantageously comprises less than 5%, preferably less than 3%, and in a preferred manner less than 2%, by weight of compounds having a number of carbon atoms that is greater than or equal to 5, and oxidized compounds, such as, for example, $CO_2$, $CO$, diethyl ether and acetaldehyde, with the percentages being expressed in terms of percentages by weight relative to the total mass of the carbon-containing compounds that are present in said effluent that is produced in said stage a).

Said isomerizing dehydration stage a) makes it possible to convert isobutanol into a mixture of butenes.

In the case where the catalyst that is used in the dehydration stage a) is a zeolitic catalyst, said catalyst comprises at least one zeolite that is selected from among the zeolites that have at least pore openings that contain 10 or 12 oxygen atoms (10 MR or 12 MR). Actually, it is known to define the size of the pores of the zeolites by the number of oxygen atoms forming the annular section of the channels of zeolites, called "member ring" or MR in English. In a preferred manner, said zeolitic catalyst comprises at least one zeolite that has a structural type that is selected from among the following structural types: MFI, FAU, MOR, FER, and BEA.

The zeolite that is used in the catalyst used in stage a) of the process according to the invention can advantageously be modified by dealuminification or desilication according to any dealuminification or desilication method that is known to one skilled in the art.

In the case where the catalyst that is used in the dehydration stage a) is an amorphous acid catalyst, said catalyst comprises at least one porous refractory oxide that is selected from among alumina, alumina activated by a deposit of mineral acid, and silica-alumina.

Said amorphous or zeolitic dehydration catalyst that is used in stage a) of the process according to the invention can also advantageously comprise at least one oxide-type matrix that is also called a binder. Matrix according to the invention is defined as an amorphous or poorly crystallized matrix.

Said matrix is advantageously selected from among the elements of the group that is formed by clays (such as, for example, among the natural clays such as kaolin and bentonite), magnesia, aluminas, silicas, silica-aluminas, aluminates, titanium oxide, boron oxide, zirconia, aluminum phosphates, titanium phosphates, zirconium phosphates, and carbon. Preferably, said matrix is selected from among the elements of the group that is formed by aluminas, silicas, and clays.

In a preferred mode, the binder has a macroporous texture as described in the patent U.S. Pat. No. 7,880,048.

The dehydration catalyst that is used in stage a) of the process according to the invention is advantageously shaped in the form of grains of different shapes and sizes. It is advantageously used in the form of extrudates that are cylindrical or multilobed, such as bilobed, trilobed, or polylobed of straight or twisted shape, but it can optionally be manufactured and employed in the form of crushed powder, tablets, rings, balls, wheels, or spheres. Preferably, said catalyst is in the form of extrudates or balls.

The isomerizing dehydration stage a) of the process according to the invention is performed at an absolute pressure at the reactor inlet of between 0.5 and 1.2 MPa, preferably between 0.6 and 1.1 MPa, and at a temperature of between 350 and 450° C. The absolute pressure at the reactor inlet is selected in such a way that said feedstock of said stage a) is in the gaseous phase at the reactor inlet.

The high operating pressure, i.e., higher than 0.5 MPa, preferably higher than 0.6 MPa, advantageously makes it possible to separate the products from the water by liquid/liquid decanting. The hourly volumetric flow rate is between 2 and 7 $h^{-1}$.

Hourly volumetric flow rate is defined as the volumetric flow rate of the feedstock at the reactor inlet in $m^3/h$ at 15° C., 1 atm divided by the volume of catalyst in $m^3$ contained in the reactor.

Said stage a) is very endothermic. It is therefore advantageously performed in at least two separate reactors, with the effluent from one reactor being heated before being sent as a feedstock for the next reactor. The temperature at the inlet of each reactor is between 350 and 450° C., preferably between 350 and 400° C., and more preferably between 350 and 375° C.

The conversion of the butanol feedstock in stage a) is advantageously greater than 95%, preferably 99%, and in a preferred manner greater than 99.8%. Conversion of the butanol feedstock is defined as the ratio of the difference between the mass flow rate of the butanol feedstock entering stage a) and the mass flow rate of the butanol feedstock leaving stage a) to the mass flow rate of the butanol feedstock entering stage a).

Stage b) for Separation of Water

In accordance with the invention, the effluent that is for the most part butylene that comes from stage a) undergoes at least one stage b) for separation of the water that is present in said effluent. The water has a negative effect on the catalysts of the subsequent stages of the process according to the invention. The effluents from stage b) are an aqueous liquid effluent, an organic liquid effluent, and optionally a gaseous effluent that comprises carbon monoxide, carbon dioxide, hydrogen, methane, and acetone, taken by itself or in a mixture. Said stage b) is preferably a decanting stage in which an aqueous phase is separated from an organic phase.

Said stage b) is advantageously performed at a pressure of between 0.5 and 1.2 MPa, preferably between 0.6 and 1.1 MPa, and at a temperature of between 35 and 60° C.

The high operating pressure of the dehydration stage a) according to the invention makes it possible to condense the water in stage b) at a high temperature. When the dehydration stage is carried out at a lower pressure, it is either necessary to use a cold cycle to condense the water or necessary to compress the effluent leaving the dehydration stage.

Purification Stage c)

In accordance with the invention, the organic liquid effluent that comes from stage b) undergoes a purification stage c) in such a way as to produce a purified organic effluent.

Said stage c) can advantageously be implemented by any method that is known to one skilled in the art, for example by a treatment in an absorption column with MDEA (methyldiethylamine) or another amine followed by a treatment on a molecular sieve, with said sieves advantageously being of the type 13X, 3A, 4A and 5A, taken by itself or in a mixture. Said stage c) can also advantageously be implemented by treatment in a column for washing with soda. Said stage c) can also advantageously be implemented by treatment of said organic effluent on a molecular sieve, with said sieves advantageously being of the type 13X, 3A, 4A and 5A, taken by itself or in a mixture. Said stage c) can also advantageously comprise a treatment on a base resin in such a way as to remove the alcohols that are present in said organic liquid effluent. Drying agents can advantageously be used in such a way as to attain a water content that is compatible with the oligomerization catalysts that are used downstream in the oligomerization stages d) and e).

The water content of said purified organic effluent is advantageously between 0 and 1,000 ppm, preferably between 0 and 500 ppm, and in a preferred manner between 0 and 200 ppm. The content of sulfur-containing components, for example $H_2S$ or COS, of said purified organic effluent is advantageously less than 100 ppm, preferably less than 50 ppm. The content of nitrogen-containing components, for example ammonia, of said purified organic effluent is less than 1 ppm. The content of inorganic components of said purified organic effluent is less than 1 ppm, preferably below the detection limit.

Stage d) for Selective Oligomerization of the Isobutenes Called "Selectopol"

In accordance with the invention, at least a portion of the purified organic effluent that comes from the purification stage c), the entire effluent that comes from the oligomerization stage g), and at least a portion of the light product that comes from the fractionation stage f) are mixed in such a way as to form a first oligomerization feedstock, with said feedstock undergoing a first stage d) for selective oligomerization of isobutenes in at least one reactor in the presence of an amorphous catalyst in such a way as to produce a first oligomerization effluent.

At least one portion of the purified organic effluent that comes from stage c) is defined as at least 50% by weight, preferably at least 90% by weight, and in a preferred manner the entire effluent that comes from said stage c), with the percentages by weight being expressed relative to the total mass of said effluent.

The conversion of the isobutene in stage d) is advantageously greater than 80%, preferably greater than 85%, and in a preferred manner greater than 90%. Conversion of the isobutene is defined as the ratio of the difference between the mass flow rate of isobutene entering stage d) and the mass flow rate of isobutene leaving stage d) to the mass flow rate of isobutene entering stage d).

The conversion of n-butenes in stage d) is advantageously less than 15%, preferably less than 10%, and in a preferred manner less than 5%. The conversion of n-butenes is defined in a manner that is analogous to the conversion of isobutene.

Said first oligomerization effluent comprises at least 50% by weight of olefins having a number of carbon atoms that is greater than or equal to 8, with the percentage by weight being expressed relative to the total mass of the olefins contained in said effluent. In particular, said effluent comprises at least 60% by weight, preferably at least 65%, and in a preferred manner at least 75% by weight, of olefins having a number of carbon atoms that is greater than or equal to 8, with the percentage by weight being expressed relative to the total mass of olefins contained in said effluent. Among the olefins that have a number of carbon atoms of greater than or equal to 8, the $C_8$-$C_{12}$ olefins are in the majority relative to the olefins that have at least 13 carbon atoms, i.e., the mass ratio of the $C_8$-$C_{12}$ olefins to the olefins that have at least 13 carbon atoms is greater than 1.

In addition to the majority presence of olefins having a number of carbon atoms that is greater than or equal to 8, the olefinic effluent produced during the first oligomerization stage d) also advantageously comprises less than 50%, preferably less than 40%, and in a preferred manner less than 35%, and in a very preferred manner less than 25% by weight of olefinic compounds of which the number of carbon atoms is less than or equal to 4, with the percentages by weight being expressed relative to the total mass of olefins contained in the effluent that is produced.

The recycling of the entire effluent that comes from the oligomerization stage g) and at least a portion of the light product that comes from the fractionation stage 0 makes it possible to improve the yield of conversion of the olefins that have less than 8 carbon atoms by a better monitoring of the exothermicity.

The olefins comprising at least 16 carbon atoms react very little in stage d) and in stage e). Their recycling upstream from stage d) makes it possible to minimize the rise in temperature, either in the reaction section of stage d) or in the reaction section of stage e). This recycling therefore makes possible a better monitoring of temperature in said reaction sections.

The catalyst that is used in the first oligomerization stage d) comprises at least one element of group VIII, preferably selected from among nickel, cobalt, iron, platinum, and palladium, and in a preferred manner, said element is nickel, and at least one porous oxide refractory substrate that is preferably selected from among alumina, silica, silica-aluminas, siliceous aluminas, zirconias, titanium oxide, magnesia, and the clays taken by themselves or in a mixture, and in a preferred manner, said substrate is an alumina or a silica-alumina, preferably a silica-alumina. In a preferred arrangement, the catalyst that is used in the first oligomerization stage d) is a silica-alumina-based catalyst as described in the patent U.S. Pat. No. 7,572,946.

Said catalyst that is used in said stage d) of the process according to the invention also advantageously comprises at least one oxide-type matrix that is also called a binder. According to the invention, matrix is defined as an amorphous or poorly-crystallized matrix.

Said matrix is advantageously selected from among the elements of the group that is formed by clays (such as, for example, from among the natural clays such as kaolin or bentonite), magnesia, aluminas, silicas, silica-aluminas, aluminates, titanium oxide, boron oxide, zirconia, aluminum phosphates, titanium phosphates, zirconium phosphates, and carbon. Preferably, said matrix is selected from among the elements of the group that is formed by aluminas, clays, and silicas; in a more preferred manner, said matrix is selected from among the aluminas, and in an even more preferred manner, said matrix is gamma-alumina.

The catalyst that is used in said stage d) of the process according to the invention is advantageously shaped in the form of grains of different shapes and sizes. It is advantageously used in the form of extrudates that are cylindrical or multilobed, such as bilobed, trilobed, or polylobed of straight or twisted shape, but can optionally be manufactured and used in the form of crushed powder, tablets, rings, balls, wheels, or spheres. Preferably, said catalyst is in the form of extrudates with sizes of between 1 and 10 mm.

Said first oligomerization stage d) of the process according to the invention is advantageously performed at a temperature of between 40 and 110° C., preferably between 60 and 90° C.; at an absolute pressure of between 0.5 and 10 MPa, preferably between 1 and 8 MPa, and in a preferred manner between 2 and 6 MPa, selected in such a way as to keep products and reagents in liquid form; and at an hourly volumetric flow rate of between 0.1 and 10 $h^{-1}$ and preferably between 0.4 and 5 $h^{-1}$.

Said first oligomerization stage d) of the process according to the invention is preferably implemented in a fixed bed. Preferably, said stage is carried out in two fixed-bed reactors in series.

Stage e) for Oligomerization of Olefins Called "Polynaphtha"

In accordance with the invention, the first oligomerization effluent that comes from stage d) undergoes a second oligomerization stage e) in the presence of an amorphous catalyst in such a way as to produce a second oligomerization effluent.

The second oligomerization stage e) makes possible the production of an olefin-enriched effluent that has a number of carbon atoms that is greater than or equal to 9.

Said second oligomerization effluent is an olefinic effluent that advantageously comprises less than 50% by weight and preferably less than 45% by weight of olefins having a number of carbon atoms of between 4 and 8 with the percentages by weight being expressed relative to the total mass of the $C_4$-$C_8$ olefinic effluent entering said second oligomerization stage e).

The conversion of isobutene in stage e) is advantageously greater than 80%, preferably greater than 85%, in a preferred manner greater than 90%, and in a very preferred manner greater than 95%.

The conversion of n-butene in stage e) is advantageously greater than 60%, preferably greater than 70%, and in a preferred manner greater than 80%.

The conversion of olefins having a number of carbon atoms of between 8 and 11 in stage e) is advantageously greater than 40%, preferably greater than 50%, and in a preferred manner greater than 60%.

The conversion of olefins having a number of carbon atoms that is at least equal to 12 in stage e) is advantageously less than 5%, preferably less than 3%, and in a preferred manner less than 1%.

The rise in temperature in the reactors due to the exothermicity of the reactions in stages d) and e) will be monitored by varying the recycling flow rate of the light product that comes from stage f) as well as the fraction of the intermediate product that comes from stage f) and is sent toward stage g).

With the n-butenes and the olefins having a number of carbon atoms at least equal to 8 being not very reactive in the first oligomerization stage d), they play the role of heat flywheel in said stage d).

With the olefins having a number of carbon atoms at least equal to 12 being not very reactive in the second oligomerization stage e), they play the role of heat flywheel in said stage e).

The catalyst that is used in stage e) of the process according to the invention has the same characteristics as the catalyst that is used in stage d) of the process according to the invention. Preferably, it is identical to the catalyst that is used in stage d) of the process according to the invention.

Said second oligomerization stage e) of the process according to the invention is advantageously performed at a temperature of between 100 and 200° C., preferably between 110 and 160° C.; at an absolute pressure of between 2 and 15 MPa, preferably between 2 and 8 MPa, and in a preferred manner between 3 and 8 MPa; and at an hourly volumetric flow rate of between 0.1 and 10 $h^{-1}$, and preferably between 0.4 and 5 $h^{-1}$. In any case, the operating pressure of the process is such that all of the reagents and products are in liquid form in the reaction zone.

Said oligomerization stage e) is advantageously implemented in at least one fixed-bed reactor, preferably at least two fixed-bed reactors in series, and more preferably at least three fixed-bed reactors in series.

The operation of stage e) at an elevated temperature makes possible the production of molecules that are less branched than if this stage were performed at a lower temperature, which leads to obtaining a product whose density is higher.

Fractionation Stage f)

In accordance with the invention, the second oligomerization effluent that comes from stage e) undergoes a fractionation stage f) in at least one distillation column in such a way as to separate said effluent into at least three products respectively corresponding to a light product for the most part comprising the $C_2$ to $C_4$ compounds, an intermediate product for the most part comprising the $C_5$ to $C_9$ compounds, corresponding to a gasoline fraction, and a middle distillate product for the most part comprising the compounds that have at least 10 carbon atoms whose fraction point is between 150 and 350° C. A bottom product that has an initial boiling point of between 350 and 370° C. is also advantageously separated. These cited products are in no way limiting.

Said light product advantageously comprises at least 80% by weight of n-butenes, preferably 85% by weight, and in a preferred manner 90% by weight, with the percentage by weight being expressed relative to the total quantity of butenes present in said light product.

At least one portion of said light product can advantageously be recycled in the first oligomerization stage d) of the process according to the invention.

At least a portion of said light product is advantageously defined as between 0 and 100% by weight of the total mass flow rate of said light product, preferably between 50 and 100% by weight, and more preferably between 75 and 100% by weight.

At least a portion of said intermediate product is treated in an oligomerization stage g).

At least a portion of said intermediate product is advantageously defined as between 80 and 100% of the total mass flow rate of said intermediate product, preferably between 90 and 100%, and more preferably between 95 and 100%.

In accordance with the invention, at least a portion of said middle distillate product is treated in a hydrogenation stage h). A portion of said middle distillate product is defined as at least 80% of the total flow rate of the middle distillate product, preferably at least 90%, and in a preferred manner the entire middle distillate product.

Said stage f) is advantageously implemented with two distillation columns operating in series, with the first distillation column fractionating the effluent that comes from the second oligomerization stage e) into a light product that for the most part comprises the $C_2$ to $C_4$ compounds and a bottom product of the first column, and the second column fractionating said bottom product of the first column into an intermediate product that for the most part comprises the $C_5$ to $C_9$ compounds and a middle distillate product for the most part consisting of compounds having at least 10 carbon atoms.

Said light product advantageously comprises at least 90% by weight of olefins whose number of carbon atoms is less than or equal to 4, preferably at least 95% by weight, more preferably at least 98% by weight, and in a preferred manner at least 99.9% by weight, with this percentage being defined relative to the total weight of said light product.

Said intermediate product advantageously comprises at least 90% by weight of olefins whose number of carbon atoms is between 5 and 9, preferably at least 96% by weight, and more preferably at least 99.8% by weight, with this percentage being defined relative to the total weight of said intermediate product.

Said middle distillate product advantageously comprises at least 90% by weight of olefins whose number of carbon atoms is at least equal to 10, preferably at least 95% by weight, more preferably at least 98% by weight, and in a preferred manner at least 99.5% by weight, with this percentage being defined relative to the total weight of said middle distillate product.

Stage g) for Oligomerization of $C_8$ Olefins Called "$C_8$ Polynaphtha"

In accordance with the invention, at least a portion of said intermediate product that is produced by stage f) of the process according to the invention is treated in a third oligomerization stage g).

The conversion of olefins having 8 carbon atoms in stage g) is advantageously between 20 and 40%. The selectivity of the oligomerization reaction of the olefins having 8 carbon atoms toward the olefins having 16 carbon atoms is greater than 95%, preferably greater than 98%, and in a preferred manner greater than 99%.

The catalyst that is used in stage g) of the process according to the invention has the same characteristics as the catalyst that is used in stage d) of the process according to the invention. Preferably, it is identical to the catalyst that is used in stage d) of the process according to the invention.

Said oligomerization stage g) of the process according to the invention is advantageously performed at a temperature of between 100 and 200° C., preferably between 110 and 160° C.; at an absolute pressure of between 2 and 15 MPa, preferably between 2 and 8 MPa, and in a preferred manner between 3 and 8 MPa; and at an hourly volumetric flow rate of between 0.1 and 5 $h^{-1}$, and preferably between 0.4 and 2 $h^{-1}$. In any case, the operating pressure of the process is such that all of the reagents and products are in liquid form in the reaction zone.

Said oligomerization stage g) is advantageously implemented in at least one fixed-bed reactor, preferably at least two fixed-bed reactors in series, and more preferably at least three fixed-bed reactors in series.

Hydrogenation Stage h)

In accordance with stage h) of the process according to the invention, at least one portion of said middle distillate product that comes from stage 0 undergoes a stage for hydrogenation of olefins into paraffins to make them able to be incorporated into the fuel pool.

Preferably, at least a portion—and preferably all—of said middle distillate product that comes from stage f) is brought into contact with a hydrogen-rich gas in the presence of a catalyst that comprises at least one metal of group VIII, advantageously selected from among palladium and nickel, taken by itself or in a mixture, and a substrate that is advantageously selected from among alumina, silica or silica-alumina.

The catalyst that is used in said hydrogenation stage h) comprises a palladium content of between 0.1 and 5% by weight and/or a nickel oxide content that is advantageously between 15 and 40% by weight relative to the total mass of the catalyst. This nickel can be promoted with molybdenum or can also be partially sulfurized. When the metal content of the catalyst increases, the operating temperature of the reaction section is to be adapted to the decrease for compensating for the increase in catalytic activity.

The hydrogenation stage h) is advantageously performed at a temperature of between 100 and 350° C. at the reactor inlet and at a pressure of between 2 and 4 MPa and at an hourly volumetric flow rate of between 1 and 5 $h^{-1}$. The molar ratio of hydrogen to hydrocarbons $H_2$/HC is between 10 and 450.

The unreacted hydrogen is separated leaving the reactor so as to be recycled as input. A fraction of the total flow of the reaction effluent from which hydrogen is removed is also recycled as input in such a way as to be used as a heat flywheel in the reaction. The flow rate of said recycled fraction represents between 2 and 5 times the mass flow rate of said portion of said middle distillate product that comes from stage f) entering stage h), i.e., before the recycling of hydrogen and said fraction.

The reactors that are used in stage h) are multi-bed reactors with a recycling of a portion of the reaction effluent for diluting the feedstock and monitoring the exotherm. The hydrogenation almost exclusively concerns olefins; the reaction is therefore very exothermic (between 100 and 300° C. of exotherm).

The performance of the hydrogenation is validated by measuring the smoke point and current gums that will advantageously be greater than 25 mm for the smoke point and less than 7 mg/100 ml for the current gum content. This is generally reflected by measuring the bromine number in accordance with the standard ASTM D2710, which is advantageously at most 10 mg of Br/100 g when these limits for the smoke point and the current gums are observed.

The effluent that comes from the optional hydrogenation stage for the most part contains hydrocarbons that can be upgraded and incorporated into the kerosene and/or diesel fuel pool, and preferably kerosene.

The hydrocarbon yield of which the number of carbon atoms is at least equal to 10 of said hydrogenation stage h) is greater than 90%, preferably greater than 95%. The olefin content in the effluent from said stage h) is between 0 and 5% of the total weight of said effluent, preferably between 0 and 2% by weight.

An optional separation stage following the hydrogenation stage h) is advantageously implemented for making possible the fractionation into a kerosene fraction and/or a diesel fuel fraction and/or a fraction having a boiling point that is higher than 360° C. and/or light fractions.

EXAMPLES

Example 1 (Compliant)

This example illustrates the invention.

Description of the Butanol Feedstock

The butanol feedstock used in the example was treated by a series of stages for distillation and for running over molecular sieves. Following these treatments, the purified feedstock has the composition that is indicated in Table 7, "stage a) feedstock" column. The purified feedstock has an ionic impurity content of less than 100 ppm, a metal content of less than 50 ppm, an oxidized impurity content of less than 150 ppm, and a total content of nitrogen-containing and sulfur-containing compounds of less than 30 ppm.

Stage a): Dehydration of the Purified Feedstock

The purified feedstock undergoes an isomerizing dehydration stage a). Said stage a) is performed at a temperature of 400° C., at a pressure of 0.85 MPa at the reactor inlet, and at an hourly volumetric flow rate of 5 $h^{-1}$ in the presence of a silica-alumina catalyst in such a way as to maximize the production of butenes.

The effluent from stage a), for the most part butylene, has the composition that is indicated in Table 7, "stage a) effluent" column. The isobutanol is converted at a level of 99.8% into a mixture of butenes that is close to thermodynamic equilibrium and into water. The reaction also produces a certain number of co-products: oxidized elements and light olefins.

Stage b): Separation of Water from the Butylenic Effluent

The effluent that is for the most part butylene and that comes from stage a) is next directed toward a decanting flask to carry out the separation of water there. The separation is carried out at 55° C. and 0.75 MPa in such a way as to promote the liquid-liquid segregation and therefore the separation of hydrocarbons from water. The residual content of water in the organic liquid effluent is then 1,800 ppm.

TABLE 1

Distribution by Mass of the Hydrocarbon-Containing Compounds in the Effluent from Stage b)

| Compound | Composition by Mass (% by Weight of Hydrocarbon-Containing Compounds) |
|---|---|
| Butane | 0.4% |
| $C_2$ Olefin | 0.6% |
| $C_3$ Olefin | 0.2% |
| $iC_4$ Olefin | 41.5% |
| $nC_4$ Olefin | 56.7% |
| Olefins having at least 5 carbon atoms | 0.6% |

The fraction of oxidized elements, nitrogen-containing elements, and water in the organic liquid effluent that comes from stage b) is 0.3%.

Stage c): Purification of the Organic Liquid Effluent

The organic liquid effluent that comes from stage b) next passes through a purification stage so as to remove the major portion of the remaining water and the compounds that can interfere with the downstream catalytic beds. This purification stage makes it possible to remove partially the sulfur-containing, nitrogen-containing, and oxidized elements remaining in a molecular sieve 13x, and then to remove partially the remaining water in a molecular sieve 3A.

The composition of the purified organic effluent leaving stage c) is indicated in Table 2:

TABLE 2

| | Composition (% by Weight) |
|---|---|
| Olefins | 99.92% |
| Water | 300 ppm |
| Nitrogen-Containing, Sulfur-Containing, and Inorganic Elements | <1 ppm |
| Oxidized Compounds | 0.05% |

Stage d): Stage for Selective Oligomerization of Isobutene

The purified organic effluent that comes from stage c) is mixed with 76.5% of the total flow of effluent from the top of the fractionation stage f) as well as all of the effluent from the oligomerization stage g) of the $C_8$ olefins. This mixture has the composition that is indicated in Table 7, "stage d) feedstock" column. It is treated in the first oligomerization stage d), which is performed in the presence of the catalyst 1811 that is marketed by Axens. The catalyst 1811 is an amorphous silica-alumina catalyst. The operating conditions of stage d) are a temperature of 60° C., a pressure of 3 MPa at the reactor inlet, and an hourly volumetric flow rate in the reactors of 2 $h^{-1}$ in such a way as to promote very heavily the oligomerization of isobutene while limiting the reaction of n-butenes.

The effluent from the oligomerization stage d) has the composition indicated in Table 7, "stage e) feedstock" column.

At the end of stage d), from 1 kg of butanol introduced into stage a), 295 g of olefins having a number of carbon atoms that is greater than or equal to 5 is produced.

Stage e): Stage for Oligomerization of Olefins

The effluent from the selective oligomerization stage d) is next treated in stage e). The latter is performed in the presence of the catalyst IP811 marketed by Axens. The operating conditions of stage e) are a temperature of 110° C., a pressure of 6 MPa at the reactor inlet, and an hourly volumetric flow rate in the reactors of 2 $h^{-1}$.

The effluent from the oligomerization stage e) has the composition that is indicated in Table 7, "stage f) feedstock" column.

Stage f): Fractionation Stage of the Oligomerization Effluents

The effluent from stage e) next undergoes a fractionation stage f) in such a way as to separate a light product that comprises the $C_2$ to $C_4$ compounds, an intermediate product comprising the $C_5$ to $C_9$ compounds, and a middle distillate product, which will constitute in part the kerosene fraction, compound of $C_{10}^+$. The distribution of the separated products is presented in Table 3.

TABLE 3

Distribution of the Products at the End of Stage f)

| Product | Composition (% by Weight) |
|---|---|
| Light Product | 4.6% |
| Intermediate Product | 44.6% |
| Middle Distillate Product | 50.8% |

From 1 kg/h of butanol entering stage a), the following are obtained: 63 g/h of light product, 618 g/h of intermediate product, and 702 g/h of middle distillate product leaving stage f). A large portion of the first two products is recycled to obtain these results: 76.5% of the light product is recycled entering stage d), and 96.5% of the intermediate product is directed toward stage g) so as to oligomerize the $C_5$-$C_8$ olefins before being redirected toward stage d).

The light product contains 500 ppm by mass of carbon-containing compounds other than $C_1$-$C_4$. The intermediate product contains 2,000 ppm by mass of carbon-containing compounds other than $C_5$-$C_9$. The middle distillate product contains 0.5% by mass of $C_1$-$C_9$ carbon-containing compounds.

Stage g): Oligomerization of the C8 Olefins 96.5% of the intermediate product that comes from stage f) is directed toward stage g) for oligomerization of the $C_8$ olefins. This stage is performed in the presence of the catalyst IP811 that is marketed by Axens. The operating conditions of stage g) are a temperature of 110° C., a pressure of 6 MPa at the reactor inlet, and an hourly volumetric flow rate in the reactors of 2 $h^{-1}$.

The composition of the effluent leaving stage g) is presented in Table 4. It is next recycled entering stage d).

TABLE 4

| Distribution by Mass of the Hydrocarbon-Containing Compounds | % by Weight |
|---|---|
| C8= | 69.9% |
| C16= | 29.9% |
| C16+ | 0.2% |

Stage h): Hydrogenation of Olefins

The middle distillate product that comes from the fractionation stage f) is directed toward stage h) for hydrogenation of olefins that is performed with a catalyst LD746 that is marketed by Axens and in which the major portion of the olefins will be hydrogenated while minimizing the production of light hydrocarbon-containing molecules. This stage is performed at a temperature of 160° C. and a pressure of 2.5 MPa at the reactor inlet. The hourly volumetric flow rate in the reaction section is 3 $h^{-1}$, and the $H_2$/HC ratio is equal to 100.

Stage h) produces a mixture of alkanes for the most part having between 9 and 16 carbon atoms whose distribution is presented in Table 5.

TABLE 5

| Composition by Mass of the Effluent from Stage h) ($H_2$ Not Included) | % by Weight |
|---|---|
| $C_{10}$-$C_{16}$ | 78.0 |
| $C_1$-$C_4$ | 1.6 |
| $C_5$-$C_9$ | 8.2 |
| $C_{16}^+$ | 12.1 |

The effluent from the hydrogenation stage h) is next fractionated, and then the corresponding fractions are mixed with the non-recycled fractions of light and intermediate products obtained from stage f).

The distribution of the products that come from the process that is performed according to Example 1 is presented in Table 6.

TABLE 6

| | % by Weight |
|---|---|
| Kerosene Fraction | 73.6% |
| Fuel Gas ($C_1$-$C_4$) | 4.3% |
| $C_5$-$C_9$ | 10.6% |
| $C_{16}^+$ | 11.4% |

Leaving stage h), from 1 kg/h of butanol entering stage a), 561 g/h of bio-kerosene is obtained.

TABLE 7

Primary Streams of Example 1

| | Feedstock from Stage a) | Effluent from Stage a) | Feedstock from Stage d) | Feedstock from Stage e) | Feedstock from Stage f) | Feedstock from Stage g) | Feedstock from Stage h) |
|---|---|---|---|---|---|---|---|
| Temperature (° C.) | 400 | 55 | 60 | 110 | 150 | 110 | 160 |
| Pressure (MPa) | 0.85 | 0.75 | 3.0 | 6.0 | 5.9 | 6.0 | 2.5 |
| Mass Flow Rate (t/h) | 16.9 | 16.9 | 23.4 | 23.4 | 23.4 | 9.9 | 11.9 |
| Composition (% by Weight) of | | | | | | | |
| Isobutanol | 69.5% | 0.1% | | | | | |
| Butane | | 0.2% | 0.8% | 0.8% | 0.8% | 0.0% | 0.0% |
| C2= | | 0.3% | 0.4% | 0.4% | 0.4% | | 0.0% |
| C3= | | 0.1% | 0.1% | 0.1% | 0.0% | | 0.0% |
| iC4= | | 21.8% | 22.6% | 2.3% | | | |
| 1C4= | | 6.2% | 33.5% | 32.5% | 3.5% | 0.2% | 0.0% |
| T2C4= | | 13.9% | | | | | |
| C2C4= | | 9.7% | | | | | |
| C5+= | | 0.3% | 0.3% | 0.3% | 0.3% | | 0.6% |
| C8= | | | 29.7% | 42.4% | 44.2% | 98.9% | 0.2% |
| C9-C11= | | | | 6.8% | 0.8% | 12.7% | |
| C12= | | | | 7.4% | 19.4% | 0.0% | 38.1% |
| C13-C15= | | | | | 1.7% | | 3.4% |
| C16= | | | | 12.7% | 13.8% | 16.6% | 32.7% |
| C16+= | | | | | 6.2% | | 12.3% |
| H2O | 29.5% | 47.3% | | | | | |
| Other Alcohols | 1% | | | | | | |

Example 2 (Non-Compliant)—Process for Production without Oligomerization of the Recycled Intermediate Product In this example, the intermediate product that comes from stage f) is recycled entering stage d) without oligomerization in a stage g).

The feedstock as well as stages a) and b) and c) are identical to Example 1.

Stage d): Stage for Oligomerization of Isobutene

The effluent that is for the most part butylene and that comes from stage c) is next mixed with 77% of the light product and 87.5% of the intermediate product that come from the fractionation stage f) and then is sent into the first oligomerization stage d), which is performed under the same operating conditions and with the same catalyst as in Example 1.

The composition of the effluent leaving the reaction is presented in Table 8.

TABLE 8

| Composition by Mass of the Effluent Leaving Stage d) | % by Weight |
|---|---|
| Butane | 0.6% |
| C2= | 0.4% |
| C3= | 0.1% |
| iC4= | 2.2% |
| nC4= | 31.3% |
| C5+= | 0.3% |
| C8= | 56.9% |
| C12= | 7.2% |
| C16= | 1.0% |

Coming from this stage, from 1 kg/h of butanol entering stage a), 295 g/h of olefins having more than 5 carbon atoms is produced.

The effluent of stage d) is next directed toward stage e) for oligomerization of olefins.

Stage e): Stage for Oligomerization of Olefins

Stage e) is performed under the same conditions and with the same catalyst as Example 1. The composition of the effluent from the second oligomerization is indicated in Table 9.

TABLE 9

| Distribution by Mass of the Hydrocarbon-Containing Compounds | % by Weight |
|---|---|
| Butane | 0.6% |
| C2= | 0.4% |
| nC4= | 3.4% |
| C5+= | 0.3% |
| C8= | 51.0% |
| C9-C11= | 6.4% |
| C12= | 23.9% |
| C13-C15= | 1.9% |
| C16= | 5.5% |
| C16+= | 6.4% |

Stage f): Stage for Fractionation of the Oligomerization Effluents

The effluent from stage e) is next fractionated into 3 products in stage f), in the same manner as in Example 1. The distribution of the separated products is presented in Table 10.

TABLE 10

| Product | % by Weight |
|---|---|
| Light Product | 4.3% |
| Intermediate Product | 51.4% |
| Middle Distillate Product | 44.3% |

From 1 kg/h of butanol entering stage a), the following are obtained: 61 g/h of light product, 733 g/h of intermediate product, and 633 g/h of middle distillate product. 77% by mass of the light product and 87.5% by mass of the intermediate product are recycled entering stage d).

The light product contains 500 ppm by mass of carbon-containing compounds other than $C_1$-$C_4$. The intermediate product contains 2,000 ppm by mass of carbon-containing compounds other than $C_5$-$C_9$. The middle distillate product contains 0.5% by mass of $C_1$-$C_9$ carbon-containing compounds.

Stage h): Hydrogenation of Olefins

The middle distillate product that comes from the fractionation stage f) is directed toward stage h) for hydrogenation of olefins. Stage h) is performed under the same conditions and with the same catalyst as Example 1. The hydrogenation effluent has the composition presented in Table 11.

TABLE 11

| Composition by Mass of the Effluent from Stage h) ($H_2$ Not Included) | % by Weight |
|---|---|
| $C_{10}$-$C_{16}$ | 66.2% |
| $C_1$-$C_4$ | 1.4% |
| $C_5$-$C_9$ | 19.9% |
| $C_{16}^+$ | 12.5% |

The effluent from the hydrogenation stage h) is next fractionated, and then the corresponding fractions are mixed with the non-recycled fractions of light and intermediate products obtained from stage f).

The distribution of the products that come from the process that is performed according to Example 2 is presented in Table 12.

TABLE 12

|  | % by Weight |
|---|---|
| Kerosene Fraction | 64.1% |
| Fuel Gas ($C_1$-$C_4$) | 4.5% |
| $C_5$-$C_9$ | 19.3% |
| $C_{16}^+$ | 12.1% |

Leaving stage h), from 1 kg/h of butanol entering stage a), 490 g of bio-kerosene is obtained.

Example 3 (Non-Compliant)—Process for Production without Recycling of the Intermediate Product In this example, neither the intermediate product nor the light product obtained from the fractionation stage f) are recycled entering the oligomerization stage d). By contrast, the intermediate product undergoes an oligomerization stage g) so as to improve the reaction yield.

The feedstock as well as stages a), b) and c) are identical to Example 1.

Stage d): Stage for Oligomerization of Isobutene

The effluent that is for the most part butylene and that comes from stage c) is next sent into the first oligomerization stage d), performed under the same operating conditions and with the same catalyst as in Example 1. The composition of the effluent leaving the reaction is presented in Table 13.

TABLE 13

| Distribution by Mass of the Hydrocarbon-Containing Compounds | % by Weight |
|---|---|
| Butane | 0.4% |
| C2= | 0.7% |
| C3= | 0.1% |
| iC4= | 4.2% |
| nC4= | 55.1% |
| C5+= | 0.5% |
| C8= | 23.4% |
| C12= | 13.6% |
| C16= | 1.9% |

At the end of this stage, from 1 kg/h of butanol entering stage a), 294 g/h of olefins having more than 5 carbon atoms is produced.

The effluent from stage d) is next directed toward stage e) for oligomerization of olefins.

Stage e): Stage for Oligomerization of Olefins

Stage e) is performed under the same conditions and with the same catalyst as Example 1. The composition of the olefinic effluent of stage e) is presented in Table 14.

TABLE 14

| Distribution by Mass of the Hydrocarbon-Containing Compounds | % by Weight |
|---|---|
| Butane | 0.4% |
| C2= | 0.7% |
| iC4= | 5.9% |
| C5+= | 0.6% |
| C8= | 39.0% |
| C9-C11= | 6.7% |
| C12= | 31.2% |
| C13-C15= | 2.0% |
| C16= | 6.7% |
| C16+= | 6.7% |

Stage f): Stage for Fractionation of the Oligomerization Effluents

The effluent from stage e) is next fractionated into 3 products in stage f), in the same manner as in Example 1. The distribution of the separated products is presented in Table 15.

TABLE 15

| Product | % by Weight |
|---|---|
| Light Product | 7.0% |
| Intermediate Product | 39.5% |
| Middle Distillate Product | 53.5% |

From 1 kg/h of butanol entering stage a), the following are obtained: 52 g/h of light product, 295 g/h of intermediate product, and 400 g/h of middle distillate product. No product is recycled in this example, contrary to what is done in Examples 1 and 2. The entire intermediate product is directed toward stage g) for oligomerization of the $C_8$ olefins so as to increase the final yield. The light product is integrated as is in the products. The middle distillate product is directed toward the hydrogenation stage h).

The light product contains 500 ppm by mass of carbon-containing compounds other than $C_1$-$C_4$. The intermediate product contains 2,000 ppm by mass of carbon-containing compounds other than $C_5$-$C_9$. The middle distillate product contains 0.5% by mass of $C_1$-$C_9$ carbon-containing compounds.

Stage g): Oligomerization of the $C_8$ Olefins

The intermediate product that comes from the fractionation stage f) is directed toward stage g). Stage g) is performed under the same conditions and with the same catalyst as in Example 1. The composition of the effluent leaving stage g) is indicated in Table 16.

TABLE 16

| Distribution by Mass of the Hydrocarbon-Containing Compounds | % by Weight |
|---|---|
| C8= | 69.9% |
| C16= | 29.9% |
| C16+ | 0.2% |

It is next directed toward stage h) for hydrogenation of olefins for reducing its content of olefins together with the middle distillate product that comes from the fractionation stage f).

Stage h): Hydrogenation of Olefins

The middle distillate product that comes from the fractionation stage f) and the effluent of stage g) are directed toward stage h) for hydrogenation of olefins. Stage h) is performed under the same conditions and with the same catalyst as Example 1. The hydrogenation effluent has the composition that is indicated in Table 17.

TABLE 17

| Composition by Mass of the Effluent from Stage h) ($H_2$ Not Included) | % by Weight |
|---|---|
| $C_{10}$-$C_{16}$ | 57.0% |
| $C_1$-$C_4$ | 1.2% |
| $C_5$-$C_9$ | 34.6% |
| $C_{16}^+$ | 7.3% |

The effluent from the hydrogenation stage h) is next fractionated, and then the corresponding fractions are mixed with the fractions of light and intermediate products obtained from stage f).

The composition leaving the hydrocarbon-containing effluent of the process is indicated in Table 18.

TABLE 18

| | % by Weight |
|---|---|
| Kerosene Fraction | 52.9% |
| Fuel Gas ($C_1$-$C_4$) | 8.3% |
| $C_5$-$C_9$ | 32.1% |
| $C_{16}^+$ | 6.7% |

Leaving stage h), from 1 kg/h of butanol entering stage a), 402 g of bio-kerosene is obtained.

Example 4 (Non-Compliant)—Process for the Production with Neither Recycling of the Intermediate Product Nor Oligomerization of Said Intermediate Product This example is similar to Example 3. However, the intermediate product does not undergo the oligomerization stage g) before being incorporated in the fuel pool.

The feedstock as well as stages a) to 0 are identical to Example 3.

The middle distillate product that comes from stage 0 is hydrogenated in stage h) for hydrogenation of olefins. The light and intermediate products that come from stage f) are directly integrated into the products of the process.

Stage h): Hydrogenation of Olefins

The middle distillate product that comes from the fractionation stage f) is directed toward stage h) for hydrogenation of olefins. Stage h) is performed under the same conditions and with the same catalyst as in Example 1.

The hydrogenation effluent has the following composition that is presented in Table 19.

TABLE 19

| Composition by Mass of the Effluent from Stage g) ($H_2$ Not Included) | % by Weight |
|---|---|
| C10-C16 | 77.7% |
| C1-C4 | 1.6% |
| C5-C9 | 8.2% |
| C16+ | 12.5% |

The effluent from the hydrogenation stage h) is next fractionated, and then the corresponding fractions are mixed with the fractions of light and intermediate products obtained from stage f).

The composition leaving the hydrocarbon-containing effluent of the process is indicated in Table 20.

TABLE 20

| | % by Weight |
|---|---|
| Kerosene Fraction | 41.8% |
| Fuel Gas ($C_1$-$C_4$) | 8.1% |
| $C_5$-$C_9$ | 43.4% |
| $C_{16}^+$ | 6.7% |

Leaving stage h), from 1 kg/h of butanol entering stage a), 319 g of bio-kerosene is obtained.

Example 5 (Non-Compliant)—Process for Production without Selective Oligomerization of Isobutenes, with Oligomerization of the Intermediate Product and Recycling In this example, the oligomerization of butenes is carried out in a single stage and not in two stages d) and e) as is taught in the invention. The more reactive i-butenes then react at the same time as the other olefins that comprise 4 to 8 carbon atoms. The feedstock as well as stages a), b) and c) are identical to Example 1.

Stage for Oligomerization of Olefins

The effluent that is for the most part butylene and that comes from stage c) is mixed with 35.7% of the light product that comes from stage 0 as well as with the entire effluent from stage g), and then it is sent into the oligomerization stage, performed in the presence of the catalyst IP811 that is marketed by Axens, at a temperature of 60° C., a pressure of 3 MPa at the reactor inlet, and an hourly volumetric flow rate of 2 $h^{-1}$. The composition of the olefinic effluent of the oligomerization stage is indicated in Table 21.

TABLE 21

| Distribution by Mass of the Hydrocarbon-Containing Compounds | % by Weight |
|---|---|
| Butane | 0.9% |
| C2= | 0.4% |
| iC4= | 5.7% |
| C5+= | 0.3% |
| C8= | 41.9% |
| C9-C11= | 6.9% |
| C12= | 17.8% |
| C13-C15= | 2.1% |
| C16= | 17.3% |
| C16+= | 6.9% |

At the end of this stage, from 1 kg/h of butanol entering stage a), 937 g/h of olefins having more than 5 carbon atoms is produced.

Stage f): Stage for Fractionation of the Oligomerization Effluents

The effluent from the oligomerization stage is next fractionated into 3 products in stage f), in the same manner as in Example 1. The distribution of the separated products is presented in Table 22.

TABLE 22

| Product | % by Weight |
|---|---|
| Light Product | 6.8% |
| Intermediate Product | 42.2% |
| Middle Distillate Product | 51.0% |

From 1 kg/h of butanol entering stage a), the following are obtained: 93 g/h of light product, 576 g/h of intermediate product, and 695 g/h of middle distillate product.

35.7% of the light product is recycled upstream from the oligomerization stage, and 100% of the intermediate product is directed toward stage g) so as to oligomerize the $C_5$-$C_8$ olefins before being recycled toward the oligomerization stage.

The light product contains 500 ppm by mass of carbon-containing compounds other than $C_1$-$C_4$. The intermediate product contains 2,000 ppm by mass of carbon-containing compounds other than $C_5$-$C_9$. The middle distillate product contains 0.5% by mass of $C_1$-$C_9$ carbon-containing compounds.

Stage g): Oligomerization of the C8=Olefins

The intermediate product that comes from the fractionation stage f) is directed toward stage g) for oligomerization of the $C_8$ olefins. Stage g) is performed under the same conditions and with the same catalyst as in Example 1. The composition of the effluent leaving stage g) is indicated in Table 23.

TABLE 23

| Distribution by Mass of the Hydrocarbon-Containing Compounds | % by Weight |
|---|---|
| C8= | 69.9% |
| C16= | 29.9% |
| C16=+ | 0.2% |

The effluent from stage g) is next recycled toward the oligomerization stage.

Stage h): Hydrogenation of Olefins

The middle distillate product that comes from the fractionation stage f) is directed toward stage h) for hydrogenation of olefins. Stage h) is performed under the same conditions and with the same catalyst as in Example 1. The hydrogenation effluent has the composition that is indicated in Table 24.

TABLE 24

| Composition by Mass of the Effluent from Stage h) (H$_2$ Not Included) | % by Weight |
|---|---|
| $C_{10}$-$C_{16}$ | 77.3% |
| $C_1$-$C_4$ | 1.6% |
| $C_5$-$C_9$ | 7.8% |
| $C_{16}^+$ | 13.3% |

The effluent from the hydrogenation stage h) is next fractionated, and then the corresponding fractions are mixed with the non-recycled fractions of light and intermediate products obtained from stage f).

The composition leaving the hydrocarbon-containing effluent of the process is indicated in Table 25.

TABLE 25

| | % by Weight |
|---|---|
| Kerosene Fraction | 71.8% |
| Fuel Gas ($C_1$-$C_4$) | 8.6% |
| $C_5$-$C_9$ | 7.3% |
| $C_{16}^+$ | 12.4% |

Leaving stage h), from 1 kg/h of butanol entering stage a), 547 g of bio-kerosene is obtained.

Synthesis of the Results of Examples 1 to 5

Table 26 compares several key results of Examples 1 to 5. The bio-kerosene yield corresponds to the quantity of bio-kerosene produced per 1 kg of butanol in the feedstock of the process.

TABLE 26

| | Example 1 In Accordance with the Base Case | Example 2 without Stage g) | Example 3 No Recycling - Oligomerization of the Intermediate Product | Example 4 No Recycling - No Oligomerization of the Intermediate Product | Example 5 A Single Oligomerization Stage |
|---|---|---|---|---|---|
| % of Converted Butenes | 98.37% | 98.10% | 93.96% | 93.96% | 94.05% |
| ΔT Stage d) | 60.2° C. | 57.0° C. | 94.3° C. | 94.3° C. | — |

TABLE 26-continued

|  | Example 1 In Accordance with the Base Case | Example 2 without Stage g) | Example 3 No Recycling - Oligomerization of the Intermediate Product | Example 4 No Recycling - No Oligomerization of the Intermediate Product | Example 5 A Single Oligomerization Stage |
|---|---|---|---|---|---|
| ΔT Stage e) | 141.0° C. | 144.0° C. | 203.0° C. | 203.0° C. | 196.0° C. |
| Bio-Kerosene Yield* | 56.15% | 48.98% | 40.24% | 31.86% | 54.76% |

*The yields include a loss of 5% in the hydrogenation of the kerosene fraction (stage h).

Example 1 shows that the exotherm in the two stages d) and e) is clearly less significant, and the kerosene yield is higher than in a case with neither recycling nor oligomerization of the intermediate product (Examples 3 and 4). Example 2 shows that the addition of stage g) makes it possible to improve the kerosene yield.

Example 5, with a single oligomerization stage but comprising the recycling of the light and intermediate products and the oligomerization of the latter, has a yield that is equivalent to Example 1, compliant. However, the percentage of converted butenes is smaller, and the monitoring of the reaction and the products that are obtained are different. Actually, the separation into two stages of the oligomerization (stages d and e) makes it possible to perform only the reactions desired in each stage and thus to monitor both the quality of the products that are obtained and the exotherms in each stage. The management of the exotherms in each stage also makes it possible to increase the service life of the catalyst (thermal stress). This impact also relates to safety (lowering the impact of a jolt on the change in composition of the feedstock). The flexibility is therefore greater.

Example 6 Additions of Aromatic Compounds and Effect on the Density

The kerosene product that is obtained in Example 1 conforms to a density of approximately 780 kg/m$^3$. Mesitylene (1,3,5-trimethylbenzene), whose density is 865 kg/m$^3$, is added to this product.

The addition of mesitylene to our kerosene up to a content of 8% by volume raises the density of the mixture to 787 kg/m$^3$.

The addition of mesitylene to our kerosene up to a content of 25% by volume raises the density to 801 kg/m$^3$.

The density limits set by the standard ASTM D7566-11a are therefore always observed even when aromatic compounds are added to the limits provided by said standard.

The invention claimed is:

1. A process for the production of middle-distillate hydrocarbon-containing bases from a butanol feedstock, with said process comprising at least:
   a) isomerizing and dehydrating said butanol feedstock in the presence of an amorphous or zeolitic acid catalyst in at least one reactor having a reactor inlet, operating at an absolute pressure at the reactor inlet of between 0.5 and 1.2 MPa and at a temperature at the reactor inlet of between 350 and 450° C. in such a way as to produce a butylenic effluent that contains water and more than 95% by weight butylene relative to the total mass of the carbon-containing compounds that are present in said butylenic effluent,
   b) separating the water that is present in said butylenic effluent at a pressure of between 0.5 and 1.2 MPa and at a temperature of between 35 and 60° C., in such a way as to produce an organic liquid effluent,
   c) purifying the organic liquid effluent that comes from b) in such a way as to produce a purified organic effluent,
   d) oligomerizing a first oligomerization feedstock in the presence of an amorphous catalyst in at least one reactor that operates at an absolute pressure of between 0.5 and 10 MPa, at a temperature of between 60 and 90° C., and at an hourly volumetric flow rate of between 0.1 and 10 h$^{-1}$, in such a way as to produce a first oligomerization effluent, comprising at least 50% by weight of olefins having a number of carbon atoms that is greater than or equal to 8, with the percentage by weight being expressed relative to the total mass of olefins contained in said first oligomerization effluent,
   e) oligomerizing said first oligomerization effluent, in the presence of an amorphous catalyst in at least one reactor that operates at an absolute pressure of between 2 and 15 MPa, at a temperature of between 100 and 200° C., and at an hourly volumetric flow rate of between 0.1 and 10 h$^{-1}$, in such a way as to produce a second oligomerization effluent,
   f) fractionating said second oligomerization effluent into at least three products which are: a light product that contains more than 50% by weight of $C_2$ to $C_4$ compounds, an intermediate product that contains more than 50% by weight of $C_5$ to $C_9$ compounds, and a middle distillate product that contains more than 50% by weight of compounds that have at least 10 carbon atoms,
   g) oligomerizing at least a portion of said intermediate product in the presence of an amorphous catalyst in at least one reactor that operates at an absolute pressure of between 2 and 15 MPa, at a temperature of between 100 and 200° C., and at an hourly volumetric flow rate of between 0.1 and 5 h$^{-1}$, to obtain a third oligomerization effluent, and
   h) hydrogenating at least a portion of said middle distillate product in the presence of a catalyst that comprises at least one metal of group VIII in at least one reactor that operates at an absolute pressure of between 2 and 4 MPa, at a temperature of between 100 and 350° C., and at an hourly volumetric flow rate of between 1 and 5 h$^{-1}$ with a hydrogen to hydrocarbon molar ratio of between 10 and 450 to obtain a hydrogenation effluent, wherein said hydrogenation effluent comprises said middle-distillate hydrocarbon-containing bases,
wherein the first oligomerization feedstock in d) comprises at least a portion of the purified organic effluent that comes from c), the entire third oligomerization effluent that comes from g), and at least a portion of the light product that comes from f).

2. The process according to claim 1, which additionally comprises purifying said butanol feedstock prior to a).

3. The process according to claim 1, in which the catalyst that is used in the isomerizing and dehydrating in a) is a zeolitic catalyst that comprises at least one zeolite that is selected from among the zeolites that have pore openings containing 10 or 12 oxygen atoms.

4. The process according to claim 1, in which the catalyst that is used in the isomerizing and dehydration in a) is an amorphous acid catalyst that comprises at least one porous refractory oxide that is selected from the group consisting of alumina, alumina activated by a deposit of mineral acid and silica-alumina.

5. The process according to claim 1, in which b) is a decanting stage in which an aqueous phase containing the water is separated from an organic phase containing the organic liquid effluent.

6. The process according to claim 1, further comprising oligomerizing between 80 and 100% by mass of said intermediate product in g).

7. The process according to claim 1, further comprising hydrogenating at least 80% by mass of the middle distillate product in h).

8. The process according to claim 1, in which f) is implemented with two distillation columns operating in series.

9. The process according to claim 1, further comprising fractionating the hydrogenation effluent into one or more of the following fractions:
 (i) a kerosene fraction;
 (ii) a diesel fuel fraction;
 (iii) a fraction having a boiling point higher than 360° C.; and
 (iv) a light fraction.

* * * * *